United States Patent [19]

Hertzog et al.

[11] 4,272,326

[45] Jun. 9, 1981

[54] ENHANCED DISTILLATION OF CYCLOHEXANOL FROM PHENOL WITH ADDITIONAL CYCLOHEXANONE FEED

[75] Inventors: Richard R. Hertzog, Morristown; David Zudkevitch, Denville, both of N.J.

[73] Assignee: Allied Chemical Corporation, Morris Township, Morris County, N.J.

[21] Appl. No.: 114,791

[22] Filed: Jan. 24, 1980

[51] Int. Cl.$^3$ .............................................. B01D 3/34
[52] U.S. Cl. ....................................... 203/62; 568/835
[58] Field of Search ........ 260/586 R, 586 P, 586 AB, 260/586 M, 589; 203/54, 62; 568/749

[56] References Cited

U.S. PATENT DOCUMENTS

| | | | |
|---|---|---|---|
| 2,857,432 | 10/1958 | Joris | 260/586 P |
| 2,873,296 | 2/1959 | Nilsson et al. | 260/586 R |
| 3,592,859 | 7/1971 | Marcell | 260/586 AB |
| 4,187,152 | 2/1980 | Roth et al. | 260/586 R |

OTHER PUBLICATIONS

Azeotropic Data-II, No. 35, Advances in Chemistry Series, ACS, 1962, p. 50.
Azeotropic Data, No. 6, Advances in Chemistry Series, ACS, 1952, p. 167.
Azeotropic Data-III; Advances in Chemistry Series 116; ACS, 1973, p. 339.

*Primary Examiner*—Frank Sever
*Attorney, Agent, or Firm*—Alan M. Doernberg; Gerhard H. Fuchs

[57] ABSTRACT

A process in which a mixture including phenol, cyclohexanone and cyclohexanol is fed to a point intermediate the top and bottom of a distillation column, an overhead stream comprising cyclohexanone and cyclohexanol is withdrawn from a point adjacent the top of the column and a bottoms stream comprising phenol is withdrawn from adjacent the bottom of the column. By feeding additional cyclohexanone to a point below where the mixture is fed, the cyclohexanone content of the bottoms is reduced. The process is useful in separating chemicals used in producing cyclohexanone from phenol for manufacturing caprolactam, a polyamide monomer, or for other purposes.

9 Claims, No Drawings

4,272,326

ENHANCED DISTILLATION OF CYCLOHEXANOL FROM PHENOL WITH ADDITIONAL CYCLOHEXANONE FEED

DESCRIPTION

BACKGROUND OF THE INVENTION

The present invention relates to the distillation of cyclohexanol from phenol and especially to the separation of mixtures of cyclohexanol, cyclohexanone and phenol into an overheads fraction comprising cyclohexanol and cyclohexanone and a bottoms fraction containing phenol, cyclohexanone and a minor proportion of cyclohexanol. Such mixtures are found in the product of the hydrogenation of phenol to produce cyclohexanone, and especially in the bottoms from a product distillation which removes the major portion of the cyclohexanone from such hydrogenation product. The bottoms from the product distillation contains a minor proportion of cyclohexanone, the unreacted phenol and the cyclohexanol which has resulted from the overhydrogenation of phenol.

Cyclohexanone is produced commercially in large quantities for manufacturing caprolactam and other purposes by a variety of processes, with the reduction of phenol and the oxidation of cyclohexane being the most common. In the hydrogenation of phenol, the cyclohexanone must be recovered from a mixture which generally includes unreacted phenol and cyclohexanol resulting from the overhydrogenation of phenol. The mixture may also contain various impurities less volatile than phenol (hereinafter called high boilers) and various solvents such as cyclohexane, benzene or hexane which are more volatile than phenol.

Since cyclohexanone is the lowest boiling major component of the mixture, it is normal to first distill the major portion of the cyclohexanone from the reaction mixture leaving a bottoms fraction comprising phenol and cyclohexanol, and usually also cyclohexanone and a minor proportion of high boilers. Conventionally, this bottoms fraction is fed to a second fractional distillation column, either in batch operation or continuously, which is designed with sufficient numbers of distillation trays or equivalent contact devices such as packing and a sufficient reflux ratio to produce an overheads fraction containing the net cyclohexanol produced, some cyclohexanone and no more than trace quantities of phenol such as below 10 ppm, preferably below 1 ppm. The bottoms stream from this second column conventionally contains substantially all of the phenol and high boilers, some cyclohexanone and substantial amounts of cyclohexanol.

In the conventional second distillation, the bottoms stream cannot be reduced in cyclohexanol content below that of the maximum boiling azeotropic mixture of cyclohexanol and phenol. In actual operations, the cyclohexanol content of the bottoms stream significantly exceeds that of the azeotropic mixture. Since this second bottoms stream is normally recycled throughout an overall cyclohexanone recovery system (e.g. by subjecting this bottoms stream to further distillation, such as extractive distillation, and returning the overhead stream to a first, product column), an incentive exists for reducing the amount of cyclohexanol in the second bottoms stream, and thereby reducing the load and energy requirements of the overall system.

The operation of the second column is normally designed to assure that the phenol content of the second overheads is minimized. While it is desirable to also minimize the cyclohexanol content of the second bottoms stream, normal manipulation of distillation conditions has limited effectiveness in reducing the cyclohexanol content of the bottoms. This is due to the attractive forces between the phenol and cyclohexanol molecules that can result in the formation of a maximum boiling azeotrope under the conditions of the second distillation. In general, the feed to the second column, which is the bottoms from the first column, is to a point intermediate between the top and bottom of the second column, and generally somewhat below the midpoint of the second column. Thus, for example, in a thirty tray fractional distillation column, the feed can be to the tenth tray from the bottom. Because cyclohexanone is the most volatile of the three major components of the mixture, it generally is found in increasing quantities going up the column and decreasing quantities going down the column. Conversely, phenol, being the least volatile of the three components is conventionally found in increasing quantities going down the column and decreasing quantities going up the column. In order to minimize phenol content in the overheads, the column is run under conditions that cause the phenol content to reach negligible amounts at the top tray. Cyclohexanol, being intermediate in volatility, is distributed along the column in a manner satisfying the overall material balance. While the exact overall distribution of the cyclohexanol in the column has not been well understood, it has been known that a significant concentration of cyclohexanol is found in the bottoms stream.

Phenol mixes with cyclohexanol and with cyclohexanone in such a manner that the intermolecular forces cause the total vapor pressure of the mixture to be lower (at equilibrium) than the level that would be present if the mixture behaved ideally. This phenomenon, referred to as a negative deviation from ideal mixing or a negative deviation from Raoult's Law, is significant enough to result in a first azeotrope (a maximum boiling binary azeotrope) between phenol and cyclohexanone (at least throughout the common pressure range for this distillation) and to result in a second azeotrope (a maximum boiling binary azeotrope) between phenol and cyclohexanol.

Several processes have been proposed to recover phenol from cyclohexanone and/or cyclohexanol by extractive distillation: adding an extraneous component to break one or both azeotropes. Such processes have the disadvantage that the extraneous component must subsequently be separated from the desired components (i.e. cyclohexanone, phenol and/or cyclohexanone) or vice versa before the desired components can be used. Such processes also generally involve adding a less volatile component to the top of a column.

BRIEF DESCRIPTION OF THE INVENTION

The present invention is an improvement in a distillation process wherein a mixture comprising phenol cyclohexanone and cyclohexanol is fed to a point intermediate the top an bottom of a distillation column, an overhead stream comprising cyclohexanone and cyclohexanol is withdrawn from a point adjacent the top of the column and a bottoms stream comprising phenol is withdrawn from adjacent the bottom of the column. The improvement comprises the step of feeding additional cyclohexanone to a point below the point where the mixture is fed, preferably to a point adjacent the bottom of the column. Almost invariably the bottoms stream contains cyclohexanol and cyclohexanone in addition to phenol. The advantageous result achieved by this additional step is that the cyclohexanol content of the bottoms stream is reduced, thus improving the overall efficiency of separation of cyclohexanol from phenol in this column.

DETAILED DESCRIPTION OF THE INVENTION

The present invention may be practiced in either a batch or a continuous distillation to separate a cyclohexanol rich overheads from a phenol rich bottom stream. It is applicable to streams containing phenol, cyclohexanone and cyclohexanol, and optionally also containing high boilers, water, organic solvents and/or other impurities. The present invention is not limited to any particular type of column or to any particular source of the mixture to be separated. Thus, for example, the present invention may be practiced with a packed column, a tray column or other fractionating device. The present invention may be practiced using a feed mixture resulting directly from the hydrogenation of phenol, or more preferably, from the bottoms of a distillation to separate the bulk of the cyclohexanone from such mixtures.

The mixture fed (as the main feed) to the column can contain any conceivable proportion of phenol and cyclohexanol and can (but need not necessarily) also contain cyclohexanone. A broad range of proportions for this mixture is about 10–70% phenol, 0 to about 50% cyclohexanone and about 0.1–90% cyclohexanol, all by moles. More commonly, the cyclohexanol content of the mixture is between about 10 and about 60 mole %. Thus a preferred range of proportions is about 20–60% phenol, about 10–40% cyclohexanone and about 10–60% cyclohexanol. It should be appreciated, however, that mixtures still higher in cyclohexanone than the above broad range may be fed if it is the direct product of phenol hydrogenation (i.e. no cyclohexanone product distillation is conducted first). In comparing mixtures, it should be recognized that weight percentages are very similar to mole percentage of phenol, cyclohexanone and cyclohexanol (molecular weights 94, 98 and 100). Components other than these three can generally be disregarded (so long as relatively minor in amounts and not substantially affecting the negative deviations from liquid phase mixing behavior of phenol-cyclohexanol and phenol-cyclohexanol) so that the above broad and narrower percentage ranges can be computed as a percentage of the total phenol, cyclohexanone and cyclohexanol only, or a percentage of the total feed.

In the above description the terms "adjacent" and "intermediate" are used in their ordinary senses as referring to near and between the extreme of, respectively. Thus a bottoms stream withdrawn from adjacent the bottom of a column is withdrawn from a low tray (or its equivalent) and preferably from the bottom of the lowermost tray (or its equivalent such as from a reboiler). Similarly, the feed of additional cyclohexanone is preferably also adjacent the bottom of the column and thus to a low tray (or its equivalent), but normally still above (albeit only slightly above) the withdrawal of the bottoms stream.

The feed of mixture intermediate the top and bottom of the column can be anywhere substantially above where the bottoms stream is withdrawn and anywhere substantially below where the overheads (and normally also reflux) are withdrawn (and reflux is returned). Normally, the spacing between this feed and the withdrawal of the overhead stream is sufficient to permit the phenol content of the vapor phase to be reduced by fractional distillation to the desired degree (e.g. under 10 or 1 ppm). In general, the greater the reflux ratio, the less this spacing must be for the same degree of phenol concentration reduction. Similarly, the spacing between the feed and the withdrawal of the bottoms stream is sufficient to permit the cyclohexanol content of the liquid phase to decrease and the phenol content of the liquid phase to increase, both by fractional distillation, to a significant extent.

It is preferred that additional cyclohexanone be fed continuously to the column, even if the rest of the distillation (especially the feed of mixture) is a batch operation. It is more preferred that both feeds (the mixture and the additional cyclohexanone) and both withdrawn streams (the overhead stream and the bottoms stream) be continuous such that the entire distillation is continuous. For example the feed may be the bottoms of a continuous first column (i.e. the cyclohexanone product column) operated continuously, and the additional cyclohexanone feed can be a portion of the overheads stream of the same first column.

In saying that additional cyclohexanone is fed to a point below where the mixture is fed, it should not be understood that this feed is necessarily cyclohexanone of extremely high purity. The advantages of the present invention are achieved so long as the additional feed contains more cyclohexanone (relative to cyclohexanol) than either the bottoms stream or the main feed mixture. Other components may be present (especially as minor impurities) in this additional feed stream. Other alcohols and ketones more volatile than cyclohexanol are suitable other components and can even, from the standpoint of phenol-cyclohexanol separation, replace part of the added cyclohexanone. It is preferred, however, that this additional feed stream consist essentially of cyclohexanone and have under 5%, more preferably under 1% cyclohexanol. Thus the additional feed in Example 7 below (i.e. Feed 2) was 99.5% cyclohexanone and 0.5% cyclohexanol. Cyclohexanone of such purity is available, for example, as the overhead stream of a first or cyclohexanone product column without further purification.

The feed of additional cyclohexanone is preferably between about 1 and 1000 percent, more preferably between about 10 and 100 percent, by moles of the phenol in the main feed.

EXAMPLES 1-5

The following five examples are based upon a detailed empirical analysis of the vapor-liquid equilibrium of the phenol-cyclohexanone-cyclohexanol system.

Representative data of this type are reported in A. K. S. Murthy et al., Inst. of Chem. Eng. "Distillation '79," Symposium Series No. 56, 1.1/51 (Rugby, England 1979); S. R. Goodwin et al., J. Chem. Eng. Data, vol. 19, no. 4, pp. 363 et seq. (1974); R. A. Muragova et al., Zhur Prikl., Khim., vol. 45, pp. 824 et seq. (1972); V. K. Engelman et al., J. Prakt., Chem., vol. 19, pp. 106 et seq. (1963); and D. R. Cova, J. Chem. Eng. Data, vol. 5, pp. 282 et seq. (1960).

The simulated flows to and from the second column are shown in Table 1. In Table 1 all quantities are given in mole parts per hour except that the phenol content of the overheads is below 1 part per million (by weight) of the total overheads.

The quantity of vapor leaving the column was 60 in Examples 1-4 and 120 in Example 5. In each Example, a reflux ratio is given (e.g. 2.39 in Example 1). The reflux ratio in Table 1 represents the portion of the condensed overheads returned to the top of the column (e.g. 42.3 in Example 1) divided by the portion of overheads removed (e.g. 17.7 in Example 1), as is conventional. The reflux ratio was computed as the minimum required to keep the phenol content of the overheads below 1 ppm.

TABLE 1

| | | Simulated Distillations | | |
|---|---|---|---|---|
| Example | Material | Feed (10th Tray) | Additional Feed | Overheads Removed | Bottoms Removed |
| 1 | Cyclohexanone | 16 | 0 | 8.54 | 7.46 |
| | Cyclohexanol | 13 | — | 9.16 | 3.84 |
| | Phenol | 25 | — | * | 25.0 |
| | Total | 54 | 0 | 17.7 | 36.3 |
| | Reflux Ratio = 2.39 | | | | |
| 2 | Cyclohenanone | 16 | 12 (10th Tray) | 17.75 | 10.25 |
| | Cyclohexanol | 12.3 | — | 9.21 | 3.09 |
| | Phenol | 25 | — | * | 25.0 |
| | Total | 53.3 | 12 | 26.96 | 38.34 |
| | Reflux Ratio = 1.22 | | | | |
| 3 | Cyclohexanone | 16 | 12 (5th Tray) | 13.38 | 14.62 |
| | Cyclohexanol | 11.7 | — | 9.12 | 2.58 |
| | Phenol | 25 | — | * | 25.0 |
| | Total | 52.7 | 12 | 22.50 | 42.20 |
| | Reflux Ratio = 1.66 | | | | |
| 4 | Cyclohexanone | 16 | 12 (1st Tray) | 11.09 | 16.91 |
| | Cyclohexanol | 11.7 | — | 9.11 | 2.59 |
| | Phenol | 25.0 | — | * | 25.0 |
| | Total | 52.7 | 12 | 20.20 | 44.50 |
| | Reflux Ratio = 1.97 | | | | |
| 5 | Cyclohexanone | 28 | 12 (1st Tray) | 15.59 | 12.41 |
| | Cyclohexanol | 11.2 | — | 10.46 | 0.74 |
| | Phenol | 25 | — | * | 25.0 |
| | Total | 52.2 | 12 | 26.5 | 38.15 |
| | Reflux Ratio = 3.60 | | | | |

*less than 1 ppm phenol by weight

These results indicate that additional cyclohexanone would lower the proportion of cyclohexanol in the bottoms from 29.5% in Example 1 (3.84 divided by 13) to 25.1% in Example 2, 22.1% in Example 3, 22.1% in Example 4 and 6.6% in Example 5. Considering the likely energy consumption and effects on column capacity as well as degree of separation (which impacts upon energy consumption and capacity of subsequent columns) Example 2 represents some improvement by adding the cyclohexanone with the main feed to the 10th plate. This is unexpected. What is even more surprising is the further improvements in Examples 3-5 where the additional cyclohexanone is fed below the main feed, especially in Examples 4 and 5 where it is fed to the first plate adjacent the bottom of the column.

EXAMPLE 6

Actual Distillation

Using a 30 tray sieve tray column equipped with reboiler and condenser, a main feed mixture of 30% cyclohexanone, 20% cyclohexanol and 50% phenol was continuously fed to the tenth tray and additional cyclohexanone in an amount 45% of the main feed by weight was fed under the bottom tray. Vapor was withdrawn from the top tray in an amount 2.5 times the main feed by weight and 80% of this vapor was returned as reflux (representing a 4 to 1 reflux ratio). Bottoms were withdrawn from the reboiler at a rate 95% of the main feed by weight. The cyclohexanone, cyclohexanol and phenol contents of the main feed, the overheads and the bottoms were determined by gas-liquid chromatography and are shown in the following Table (all quantities are weight percentages except as indicated):

| | Main Feed | Overheads | Bottoms |
|---|---|---|---|
| Cyclohexanone | 30 | 62 | 44 |
| Cyclohexanol | 20 | 38 | 2 |
| Phenol | 50 | 8 ppm | 54 |

When the same still was operated without the additional feed of cyclohexanone (at a reflux ratio of 4 to 1), the streams were as shown in the following Table:

| | Main Feed | Overheads | Bottoms |
|---|---|---|---|
| Cyclohexanone | 27.5 | 50 | 21 |
| Cyclohexanol | 23.5 | 50 | 15 |
| Phenol | 49 | 10 ppm | 64 |

These results indicate that adding additional cyclohexanone to the bottom of the column resulted in removal of over 80% of the cyclohexanol that was in the bottoms stream without the additional cyclohexanone feed.

EXAMPLE 7

Actual Distillation

In Experiment A, a liquid mixture called herein "Feed-1" containing 14 wt % of cyclohexanone, 41 wt % cyclohexanol, 35 wt % of phenol and 10 wt % of "high boilers" was fed continuously into the 10th tray, counted from the bottom, of an Oldershaw column assembly which consisted of a reboiler, 35 trays, a condenser and a reflux splitter. Another stream called herein "Feed-2" comprised of cyclohexanone was fed continuously at the same time as Feed 1 to above the first tray, counted from the bottom, of the same column. Part of the vapor condensate was withdrawn as the overhead product and part was returned as reflux to the top tray of the column. A ratio of the reflux stream to the overhead product (i.e. the reflux ratio) of 3.5:1 was kept constant throughout the entire operation.

The column was run for several hours at the absolute pressure of 27 kPa (200 mm Hg) measured at the condenser and samples were taken and analyzed. These data, shown in Table 2 below, indicate that enhanced recovery of cyclohexanol in the overhead product was achieved by application of this invention.

Another experiment, Experiment B in Table 2, was carried out distilling the same "Feed 1" with the same apparatus under the same conditions, but without "Feed 2". The results, also shown in Table 2, clearly indicated that conventional distillation leaves a significant amount of cyclohexanol in the bottoms stream, thus providing the incentive for this invention. A comparison of Experiment A with Experiment B shows that the cyclohexanol content of the bottoms stream was reduced more than ten-fold.

In Table 2, all concentrations are by weight % unless otherwise indicated. All flow rates are in parts by volume. Pressures are given in kiloPascals with pressures in millimeters of mercury shown in parenthesis.

TABLE 2

|  | Feed 1 | Feed 2 | Overhead | Bottoms |
|---|---|---|---|---|
| Experiment A (Reflux Ratio 3.5:1) | | | | |
| Cyclohexanone (%) | 14 | 99.5 | 39.79 | 37.51 |
| Cyclohexanol (%) | 41 | 0.5 | 60.21 | 2.09 |
| Phenol (%) | 35 | 0 | <10 ppm | 46.97 |
| High Boilers (%) | 10 | 0 | ND | 13.43 |
| Tray (from bottom) | 10 | 1 | 35 | 0 |
| Pressure | 99.6 | 99.6 | 27 | NM |
|  | (747) | (747) | (200) |  |
| Rate (volume parts) | 25.0 | 10.0 | 16.36 | 18.64 |
| Experiment B (Reflux Ratio 3.5:1) | | | | |
| Cyclohexanone (%) | 14 | — | 32.51 | 2.8 |
| Cyclohexanol (%) | 41 | — | 67.49 | 25.1 |
| Phenol (%) | 35 | — | <10 ppm | 56.2 |
| High Boilers | 10 | — | ND | 15.9 |
| Tray (from bottom) | 10 | — | 35 | 0 |
| Pressure | 99.6 | — | 27 | NM |
|  | (747) |  | (200) |  |
| Rate (volume parts) | 25 | — | 9.42 | 155.8 |

ND = none detected
NM = not measured

We claim:

1. In a distillation process wherein a mixture comprising phenol, cyclohexanone and cyclohexanol is fed to a point intermediate the top and bottom of a distillation column, an overhead stream comprising cyclohexanone and cyclohexanol is withdrawn from a point adjacent the top of the column and a bottoms stream comprising phenol is withdrawn from adjacent the bottom of the column; the improvement which comprises feeding A stream consisting essentially of cyclohexanone to a point below the point where the mixture is and in an amount sufficient to cause the cyclohexanol content of the bottoms stream to be reduced below the proportion of cyclohexanol in the azeotrope of cyclohexanol and phenol.

2. The distillation process of claim 1 wherein the additional cyclohexanone is fed adjacent to bottom of the column.

3. The distillation process of claim 1 or claim 2 wherein the additional cyclohexanone is fed continuously to the column.

4. The distillation process of claim 1 or claim 2 wherein the feeds of mixture and of additional cyclohexanone and the withdrawal of bottoms and of overheads are all continuous.

5. The distillation process of claim 1 or claim 2 wherein the mixture comprises, by moles, between about 10 and 70 percent phenol, between 0 and about 50 percent cyclohexanone and between about 0.1 and 90 percent cyclohexanol.

6. The distillation process of claim 5 wherein additional cyclohexanone is fed at a rate between about 1 and 1000 percent, by moles of the phenol.

7. The distillation process of claim 1 or claim 2 wherein the mixture comprises, by moles, between about 20 and 60 percent phenol, between about 10 and 40 percent cyclohexanone and between about 10 and 60 percent cyclohexanol.

8. The distillation process of claim 7 wherein the additional cyclohexanone is fed at a rate between about 10 and about 100 percent, by moles of the phenol.

9. The distillation process of claim 1 or 2 wherein additional cyclohexanone is fed as a stream consisting essentially of cyclohexanone.

* * * * *